United States Patent [19]
Graham et al.

[11] Patent Number: 5,998,407
[45] Date of Patent: *Dec. 7, 1999

[54] INHIBITORS OF FARNESYL-PROTEIN TRANSFERASE

[75] Inventors: Samuel L. Graham, Schwenksville; John S. Wai, Harleysville; Neville J. Anthony, Hatfield, all of Pa.

[73] Assignee: Merck & Co., Inc., Rahway, N.J.

[*] Notice: This patent is subject to a terminal disclaimer.

[21] Appl. No.: 09/164,741

[22] Filed: Oct. 1, 1998

Related U.S. Application Data

[63] Continuation of application No. 08/823,920, Mar. 25, 1997, Pat. No. 5,852,010
[60] Provisional application No. 60/014,594, Apr. 3, 1996.

[51] Int. Cl.$^6$ ........................ C07D 843/24; A61K 31/395
[52] U.S. Cl. ........................ 514/221; 540/504; 540/509
[58] Field of Search ............................. 514/221; 540/504, 540/509

[56] References Cited

U.S. PATENT DOCUMENTS

| | | | |
|---|---|---|---|
| 5,532,359 | 7/1996 | Marsters et al. | 540/522 |
| 5,550,126 | 8/1996 | Horwell et al. | 514/237.5 |
| 5,578,629 | 11/1996 | Ciccarone et al. | 514/397 |
| 5,595,990 | 1/1997 | Baldwin et al. | 514/221 |
| 5,618,812 | 4/1997 | Castro Pineiro et al. | 514/221 |
| 5,631,251 | 5/1997 | Butcher et al. | 514/221 |
| 5,852,010 | 12/1998 | Grahma et al. | 514/221 |

FOREIGN PATENT DOCUMENTS

WO 95/32191 11/1995 WIPO.
WO 96/30343 10/1996 WIPO.

OTHER PUBLICATIONS

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Graham, S.L., "Inhibitors of protein farnesylation: a new approach to cancer chemotherapy," Exp. Opin. Ther. Patents vol. 5 (12), pp. 1269–1285 (1995).

Graham, S.L. and Williams, Theresa M., "Inhibitors of protein franesylation," Exp. Opin. ther. Patents, vol. 6 (12), pp. 1295–1304 (1996).

James, G.L. et al., "Benzodiazepine Peptidomimetic BZA–5B Interrupts the MAP Kinase Activation Pathway in H–Ras–transformed Rat–1 Cells, but Not in Ultransformed Cells," The Journal of Biological Chemistry, vol. 269, No. 44, pp. 27705–27714 (1994).

James, G. L. et al., "Benzodiazepine Peptidomimetics: Potent Inhibitors of Ras Farnesylation in Animal Cells," Science, vol. 260 pp. 1937–1942 (1993).

James, G., et al., "Polylysine and CVIM Sequences of K–RasB Dictate Specificity of Prenylation and Confer Resistance to Benzodiazepine Peptidomimetic in Vitro," The Journal of Biological Chemistry, vol. 270, No. 11, pp. 6221–6226 (1995).

Kohl, N.E. et al., "Selective Inhibition of ras–Dependent Transformation by a Farnesyltransferase Inhibitor", Science, vol. 260, pp. 1934–1937 (1993).

Kohl, N.E. et al.,"Protein farnesyltrasferase inhibitors block the growth of ras–dependent tumors in nude mice", Proc. Natl. Acad. Sci. USA, Med Sciences, vol. 91, pp. 9141–9145 (1994).

Kohl, N.E., et al., "Inhibition of farnesyltransferase induces regression of mammary and salivary carcinomas in ras transgenic mice," Nature Medicine, vol. 1, No. 8, pp. 792–797 (1995).

Marsters, J.C., et al., "Benzodiazepine Peptidomimetic Inhibitors of Farnsyltransferase," Bioorganic & Medicinal Chemistry, vol. 2, No. 9, pp. 949–957 (1994).

Sepp–Lorenzino L., et al., "A Peptidomimetic Inhibitor of Farnesyl:Protein Transferase Blocks the Anchorage–dependent and–independent Growth of Human Tumor Cell Lines," Cancer Research, vol. 55, 5302–5309 (1995).

*Primary Examiner*—Mukund J. Shah
*Assistant Examiner*—Deepak R. Rao
*Attorney, Agent, or Firm*—Dianne Pecoraro; Mark R. Daniel

[57] ABSTRACT

The present invention is directed to substituted benozdiazepine compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

13 Claims, No Drawings

INHIBITORS OF FARNESYL-PROTEIN TRANSFERASE

This is a continuation of application Ser. No. 08/823,920 filed Mar. 25, 1997 now U.S. Pat. No. 5,852,010, which claims the benefit of Provisional Application No. 60/014,594 filed Apr. 3, 1996.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that FPTase inhibitors are inhibitors of proliferation of vascular smooth muscle cells and are therefore useful in the prevention and therapy of arteriosclerosis and diabetic disturbance of blood vessels (JP H7-112930).

It is, therefore, an object of this invention to develop peptidomimetic compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises peptidomimetic benzodiazepine-containing compounds which inhibit the farnesyl-protein transferase. The instant compounds lack a thiol moiety and thus offer unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

The compounds of this invention are illustrated by the formula:

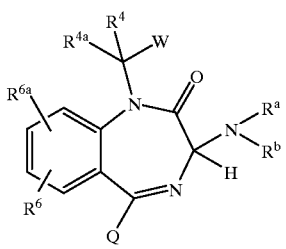

(I)

DETAILED DESCRIPTION OF THE INVENTION

The compounds of this invention are useful in the inhibition of farnesyl-protein transferase and the farnesylation of the oncogene protein Ras. In one embodiment of this invention, the inhibitors of farnesyl-protein transferase are illustrated by the formula:

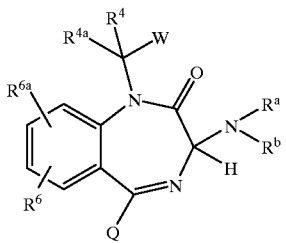

(I)

wherein:

$R^a$ is

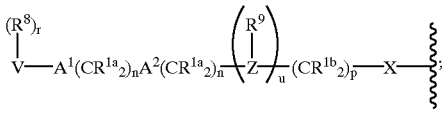

$R^b$ is selected from:
 a) hydrogen,
 b) aryl, heterocycle, $C_3$–$C_{10}$ cycloalkyl, $C_2$–$C_6$ alkenyl, $C_2$–$C_6$ alkynyl, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
 c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^{1a}$ and $R^{1b}$ are independently selected from:
 a) hydrogen,
 b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
 c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^2$ is selected from
 a) hydrogen,
 b) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^3$ is selected from a sidechain of a natural amino acid;

$R^4$ and $R^{4a}$ are independently selected from:
 a) hydrogen,
 b) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^5$ is selected from:
 a) tetrazole,
 b) $CO_2R^{10}$, and
 c) $CONR^{10}R^{10}$;

$R^6$ and $R^{6a}$ are independently selected from:
 a) hydrogen,
 b) halogen,
 c) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^8$ is selected from:
 a) hydrogen,
 b) aryl, heterocycle, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—$C(NR^{10})$—, $R^{10}C(O)$—, $R^{10}OC(O)$—, $N_3$, —$N(R^{10})_2$, or $R^{11}OC(O)NR^{10}$—, and
 c) $C_1$–$C_6$ alkyl unsubstituted or substituted by aryl, heterocycle, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
 a) hydrogen,
 b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}C(O)$—, $R^{10}OC(O)$—, $N_3$, —$N(R^{10})_2$, or $R^{11}OC(O)NR^{10}$—, and
 c) $C_1$–$C_6$ alkyl unsubstituted or substituted by perfluoroalkyl, F, Cl, Br, $R^{10}O$—, $R^{11}S(O)_m$—, $R^{10}OC(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is selected from hydrogen, $C_1$–$C_6$ alkyl, benzyl and aryl;

$R^{11}$ is selected from $C_1$–$C_6$ alkyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

Q is selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, R$^{10}$O—, R$^{11}$S(O)$_m$—, R$^{10}$C(O)NR$^{10}$—, (R$^{10}$)$_2$N—C(O)—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—,
 c) unsubstituted or substituted $C_1$–$C_6$ alkyl wherein the substitutent on the substituted $C_1$–$C_6$ alkyl is selected from unsubstituted or substituted aryl, heterocyclic, halogen $C_3$–$C_{10}$ cycloalkyl, $C_2$–$C_6$ alkenyl, $C_2$–$C_6$ alkynyl, R$^{10}$—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

V is selected from:
 a) hydrogen,
 b) heterocycle,
 c) aryl,
 d) $C_1$–$C_{20}$ alkyl wherein from 0 to 4 carbon atoms are replaced with a heteroatom selected from O, S, and N, and
 e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$;

W is selected from:
 a) hydrogen,
 b) CF$_3$,
 c) unsubstituted or substituted $C_1$–$C_8$ alkyl wherein the substitutent on the substituted $C_1$–$C_8$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;
 d) unsubstituted or substituted $C_1$–$C_8$ cycloalkyl wherein the substitutent on the substituted $C_1$–$C_8$ cycloalkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;
 e) unsubstituted or substituted heterocycle,
 f) unsubstituted or substituted aryl, and
 g) CON(R$^2$)CR$^3$R$^5$,
or R$^4$, R$^{4a}$ and W taken together are hydrogen;

X is —CH$_2$—, —C(=O)—, or —S(=O)$_m$—;

Z is a heterocycle;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or the pharmaceutically acceptable salts thereof.

In a preferred embodiment of this invention, the Ras farnesyl transferase inhibitors of formula I contain the following substituents:

$R^b$ is selected from:
 a) hydrogen, and
 b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

$R^3$ is selected from the side chain of methionine, serine, glutamine, leucine and phenylalanine;

$R^4$ and R4a are independently selected from:
 a) hydrogen, and
 b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—;

$R^5$ is selected from:
 a) CO$_2$R$^{10}$, wherein R$^{10}$ is hydrogen or $C_1$–$C_6$ alkyl and
 b) CONR$^{10}$R$^{10}$, wherein R$^{10}$ is hydrogen or $C_1$–$C_6$ alkyl.

Q is selected from:
 a) hydrogen
 b) substituted or unsubstituted aryl, $C_3$–$C_{10}$ cycloalkyl, R$^{10}$O—, R$^{11}$S(O)$_m$—, R$^{10}$C(O)NR$^{10}$—, (R$^{10}$)$_2$N—C(O)—, CN, NO$_2$, (R$^{10}$)$_2$N—C(NR$^{10}$)—, R$^{10}$C(O)—, R$^{10}$OC(O)—, —N(R$^{10}$)$_2$, or R$^{11}$OC(O)NR$^{10}$—,
 c) unsubstituted or substituted $C_1$–$C_6$ alkyl wherein the substitutent on the substituted $C_1$–$C_6$ alkyl is selected from unsubstituted or substituted aryl, heterocyclic, halogen, $C_3$–$C_{10}$ cycloalkyl, $C_2$–$C_6$ alkenyl, $C_2$–$C_6$ alkynyl, R$^{10}$O—, R$^{11}$S(O)$_m$—, R$^{10}$C(O)NR$^{10}$—, (R$^{10}$)$_2$N—C(O)—, CN, (R$^{10}$)$_2$N—C(NR$^{10}$)—, R$^{10}$C(O)—, R$^{10}$OC(O)—, N$_3$, —N(R$^{10}$)$_2$, and R$^{11}$OC(O)—NR$^{10}$—; and X is —CH$_2$—;

or the pharmaceutically acceptable salts thereof.

A preferred embodiment of the compounds of this invention are illustrated by the formula A:

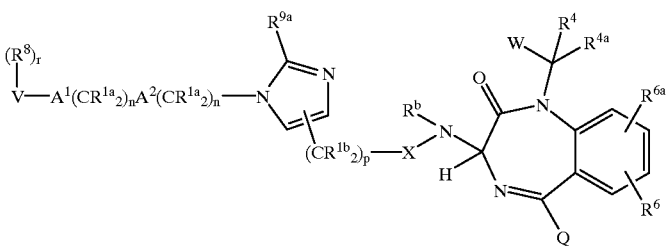

A wherein:
$R^b$ is selected from:
a) hydrogen, and
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^3$ is selected from the side chain of methionine, serine, glutamine, leucine and phenylalanine;

$R^4$ and R4a are independently selected from:
a) hydrogen, and
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^5$ is selected from:
a) $CO_2R^{10}$, wherein $R^{10}$ is hydrogen or $C_1$–$C_6$ alkyl and
b) $CONR^{10}R^{10}$, wherein $R^{10}$ is hydrogen or $C_1$–$C_6$ alkyl.

$R^{9a}$ is hydrogen or methyl;

Q is selected from:
a) hydrogen
b) substituted or unsubstituted aryl, $C_3$–$C_{10}$ cycloalkyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, halogen, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—; and X is —$CH_2$—;

or the pharmaceutically acceptable salts thereof.

In a more preferred embodiment of this invention, the inhibitors of farnesyl-protein transferase are illustrated by the formula B:

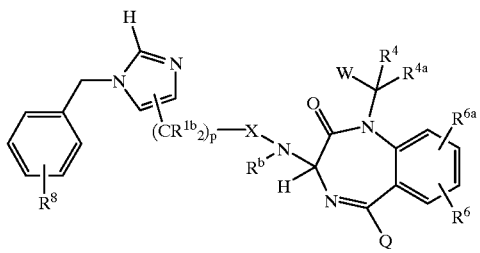

B wherein:
$R^b$ is selected from:
a) hydrogen, and
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^3$ is selected from methionine, serine, glutamine, leucine and phenylalanine;

$R^4$ and R4a are independently selected from:
a) hydrogen, and
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^5$ is selected from:
a) $CO_2R^{10}$, wherein $R^{10}$ is hydrogen or $C_1$–$C_6$ alkyl and
b) $CONR^{10}R^{10}$, wherein $R^{10}$ is hydrogen or $C_1$–$C_6$ alkyl.

$R^8$ is selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—,
d) unsubstituted or substituted aryl or heterocycle;

Q is selected from:

a) hydrogen b) substituted or unsubstituted aryl, $C_3$–$C_{10}$ cycloalkyl, $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, halogen, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—; and X is —$CH_2$—;

or the pharmaceutically acceptable salts thereof.

In a second more preferred embodiment of this invention, the inhibitors of farnesyl-protein transferase are illustrated by the formula C:

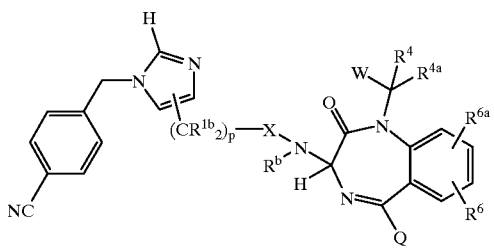

C wherein:

$R^b$ is selected from:
a) hydrogen, and
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^3$ is selected from the side chain of methionine, serine, glutamine, leucine and phenylalanine;

$R^4$ and R4a are independently selected from:
a) hydrogen, and
b) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^5$ is selected from:
a) $CO_2R^{10}$, wherein $R^{10}$ is hydrogen or $C_1$–$C_6$ alkyl and
b) $CONR^{10}R^{10}$, wherein $R^{10}$ is hydrogen or $C_1$–$C_6$ alkyl;

Q is selected from:
a) hydrogen b) substituted or unsubstituted aryl, $C_3$–$C_{10}$ cycloalkyl, $R^{10}O$—, $R^{11}S(O)_m$—, $R^{10}C(O)NR^{10}$—, $(R^{10})_2N$—C(O)—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, halogen, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—; and X is —$CH_2$—;

or the pharmaceutically acceptable salts thereof.

The preferred compounds of this invention include

3(R)-3-[1-(4-Cyanobenzyl)imidazol-5-yl-methylamino]-5-phenyl-1-(2,2,2-trifluoroethyl)-H-benzo[e][1,4]diazepine-2-one;

3(S)-3-[1-(4-Cyanobenzyl)imidazol-5-yl-methylamino]-5-phenyl-1-(2,2,2-trifluoroethyl)-H-benzo[e][1,4]diazepine-2-one;

3(R)-3-[1-(4-Cyanobenzyl)imidazol-5-yl-acetylamino]-5-phenyl-1-(2,2,2-trifluoroethyl)-H-benzo[e][1,4]diazepine-2-one;

3(S)-3-[1-(4-Cyanobenzyl)imidazol-5-yl-acetylamino]-5-phenyl-1-(2,2,2-trifluoroethyl)-H-benzo[e][1,4]diazepine-2-one;

3(R,S)-3-[1-(4-Cyanobenzyl)imidazol-5-yl-acetylamino]-5-phenyl-1-(4-methoxy benzyl)-H-benzo[e][1,4]diazepine-2-one;

3(R)-3-[1-(4-Cyanobenzyl)imidazol-5-yl-acetylamino]-5-phenyl-1-(methyl)-H-benzo[e][1,4]diazepine-2-one;

3(R)-3-[1-(4-Cyanobenzyl)imidazol-5-yl-acetylamino]-5-(4-fluorophenyl-1-(2,2,2-trifluoroethyl)-H-benzo[e][1,4]diazepine-2-one;

3-[5-Oxo-pyrrolidine-2(S)-carbonylamino]-2,3-dihydro-2-oxo-5-phenyl-1H-1,4-benzodiazepine-2-one;

3(R)-3-[1-(4-Cyanobenzyl)imidazol-5-yl-ethylamino]-5-phenyl-1-(2,2,2-trifluoroethyl)-H-benzo[e][1,4]diazepine-2-one; and 3(S)-3-[1-(4-Cyanobenzyl)imidazol-5-yl-ethylamino]-5-phenyl-1-(2,2,2-trifluoroethyl)-H-benzo[e][1,4]diazepine-2-one.

Specific examples of the compounds of the invention include

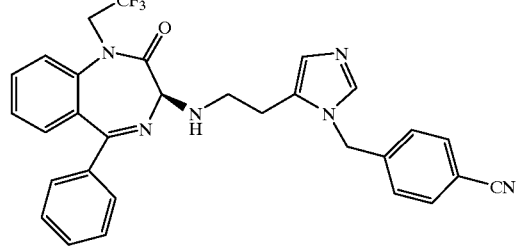

3(S)-3-[1-(4-Cyanobenzyl)imidazol-5-yl-ethylamino]-5-phenyl-1-(2,2,2-trifluoroethyl)-H-benzo[e][1,4]diazepine-2-one; and

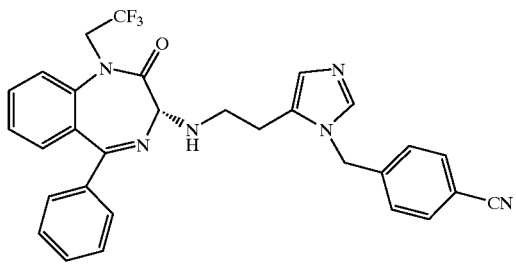

3(R)-3-[1-(4-Cyanobenzyl)imidazol-5-yl-ethylamino]-5-phenyl-1-(2,2,2-trifluoroethyl)-H-benzo[e][1,4]diazepine-2-one.

In the present invention, the amino acids which are disclosed are identified both by conventional 3 letter and single letter abbreviations as indicated below:

| Alanine | Ala | A |
| --- | --- | --- |
| Arginine | Arg | R |
| Asparagine | Asn | N |
| Aspartic acid | Asp | D |
| Asparagine or Aspartic acid | Asx | B |
| Cysteine | Cys | C |
| Glutamine | Gln | Q |
| Glutamic acid | Glu | E |
| Glutamine or Glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, hienofuryl, thienothienyl, and thienyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1$–$C_6$ alkyl$)_2$, $NO_2$, CN, $(C_1$–$C_6$ alkyl)O—, —OH, $(C_1$–$C_6$ alkyl)S(O)$_m$—, $(C_1$–$C_6$ alkyl)C(O)NH—, $H_2$N—C(NH)—, $(C_1$–$C_6$ alkyl)C(O)—, $(C_1$–$C_6$ alkyl)OC(O)—, $N_3$, $(C_1$–$C_6$ alkyl)OC(O)NH— and $C_1$–$C_{20}$ alkyl.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{10}$, Z, n, etc.) at a particular location in a molecule be independent of its definitions elsewhere in that molecule. Thus, —$N(R^{10})_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "*The Peptides*", Vol. I, Academic Press 1965, or Bodanszky et al., "*Peptide Synthesis*", Interscience Publishers, 1966, or McOmie (ed.) "*Protective Groups in Organic Chemistry*", Plenum Press, 1973, or Barany et al., "*The Peptides: Analysis, Synthesis, Biology*" 2, Chapter 1, Academic Press, 1980, or Stewart et al., "Solid Phase Peptide Synthesis", Second Edition, Pierce Chemical Company, 1984. The teachings of these works are hereby incorporated by reference.

Abbreviations used in the description of the chemistry and in the Examples that follow are:

| | |
|---|---|
| Ac$_2$O | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-HCl; |
| HOBT | 1-Hydroxybenzotriazole hydrate; |
| Et$_3$N | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

Compounds of this invention are prepared by employing the reactions shown in Reaction Schemes 1 to 6 in addition to other standard manipulations such as ester hydrolysis, cleavage of protecting groups, etc., as may be known in the literature or exemplified in the experimental procedures.

SCHEME 1

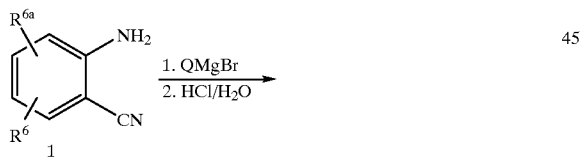

SCHEME 2

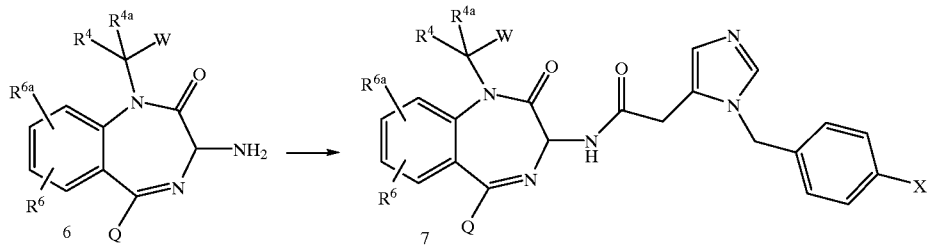

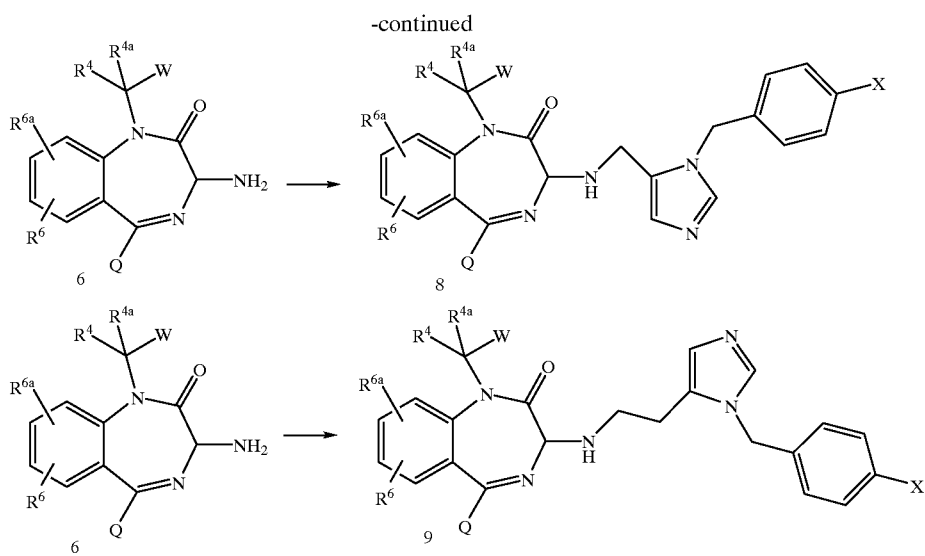
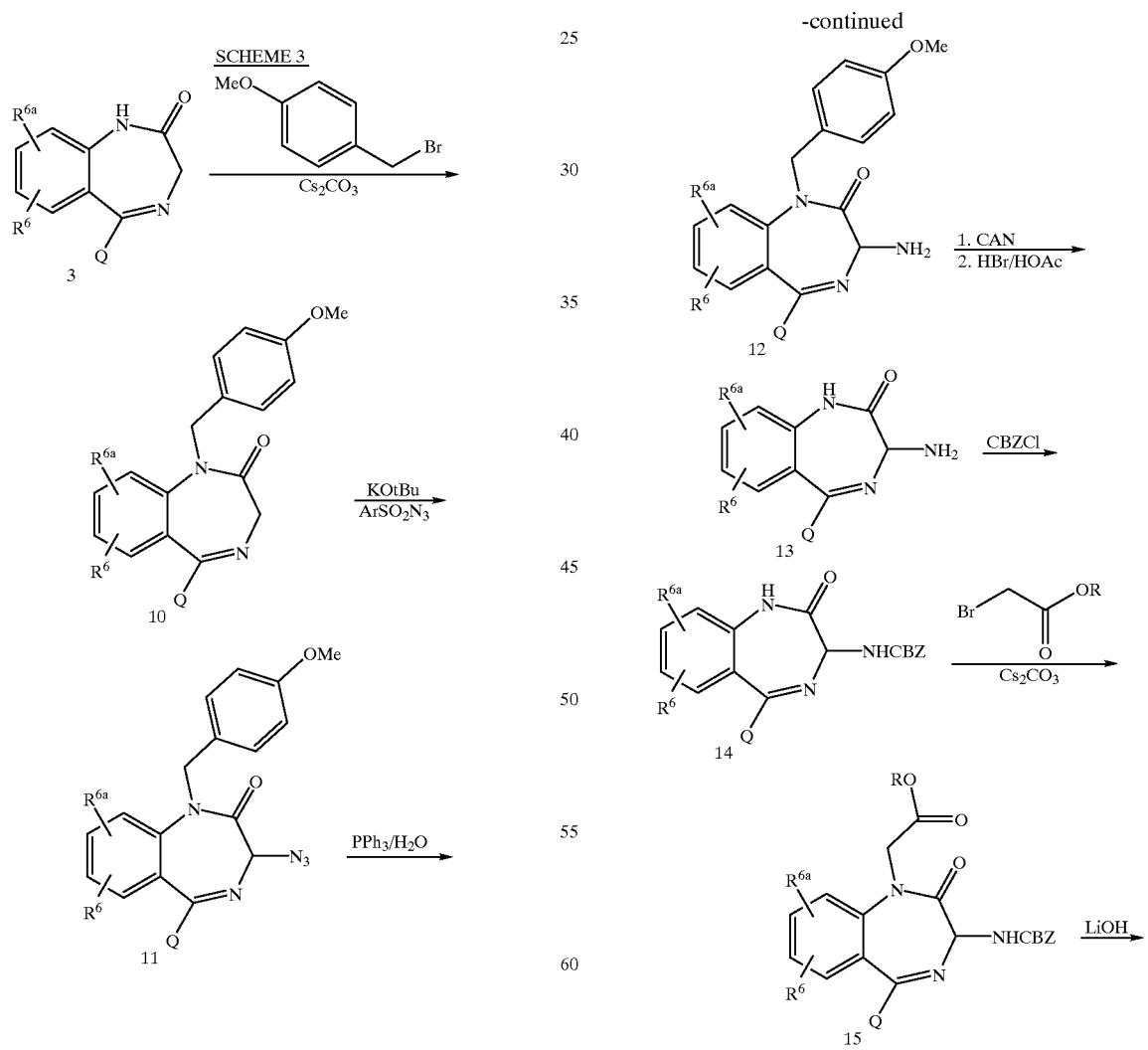

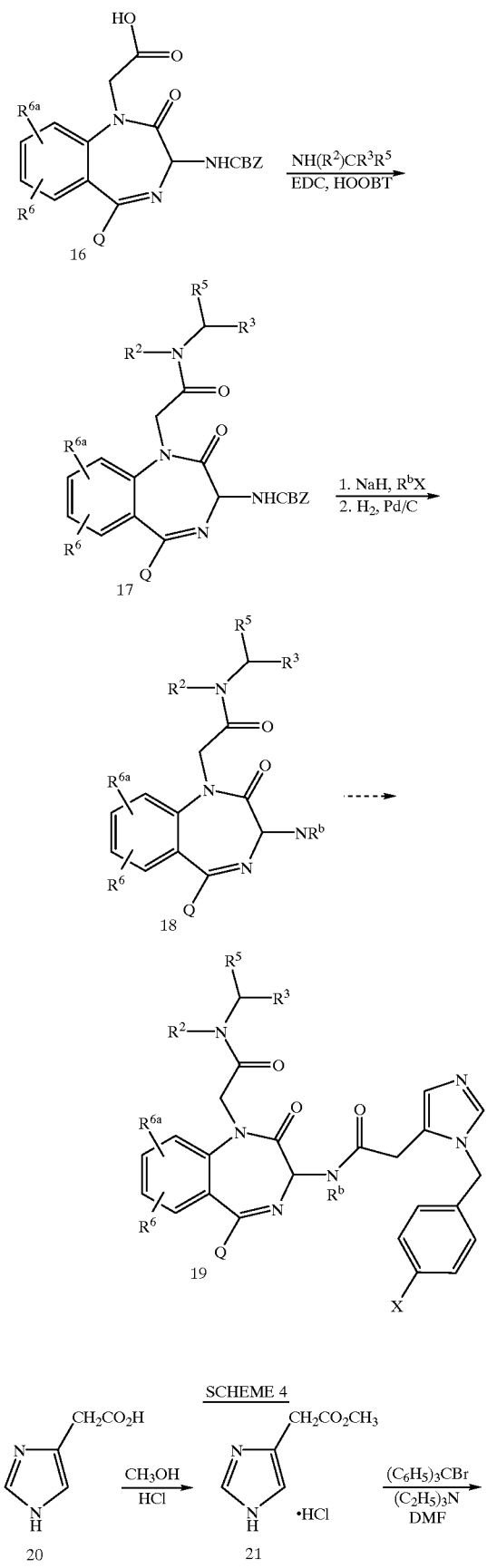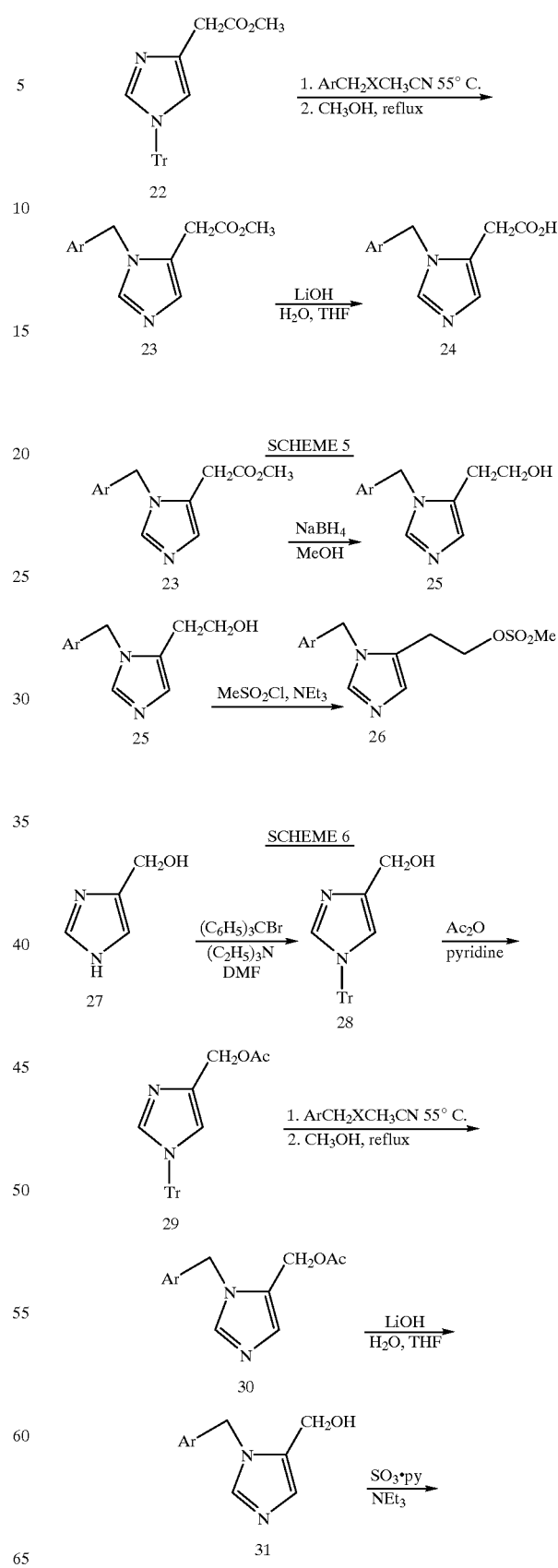

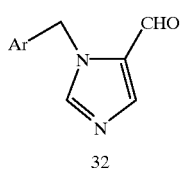
REACTION SCHEME 7
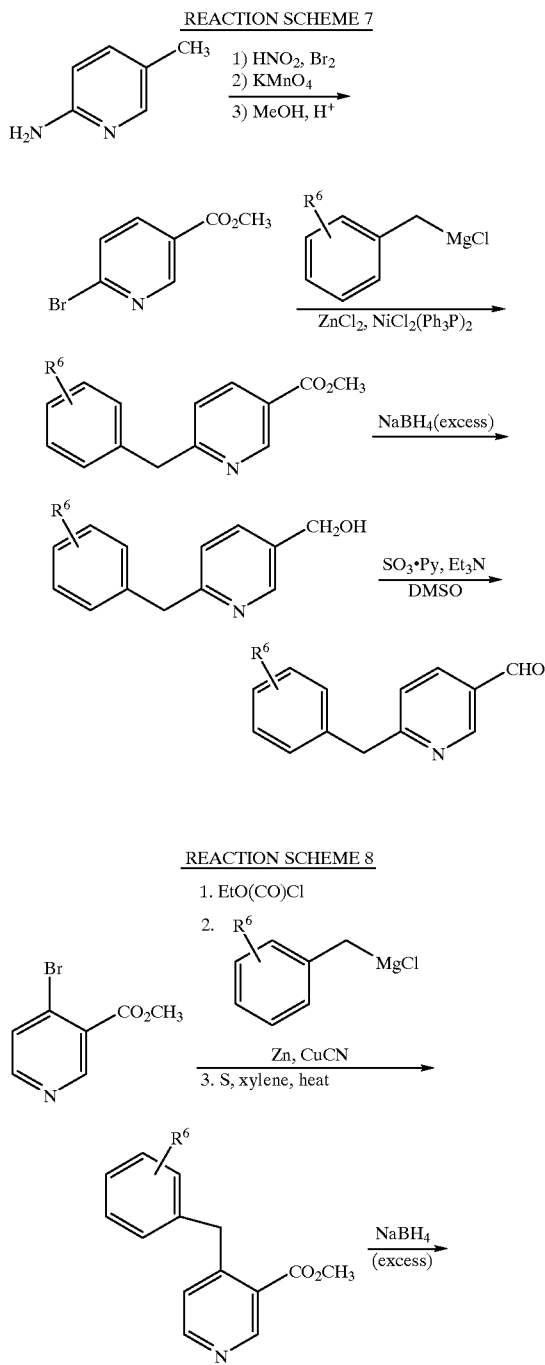
REACTION SCHEME 8
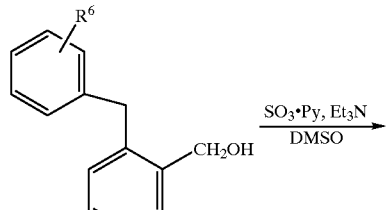
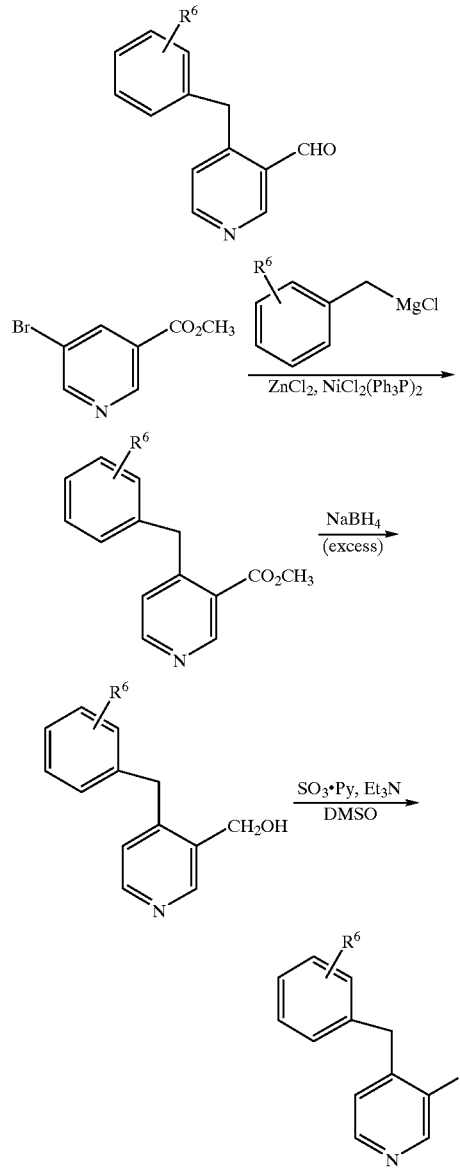
REACTION SCHEME 9
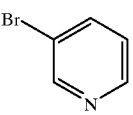
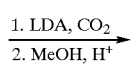

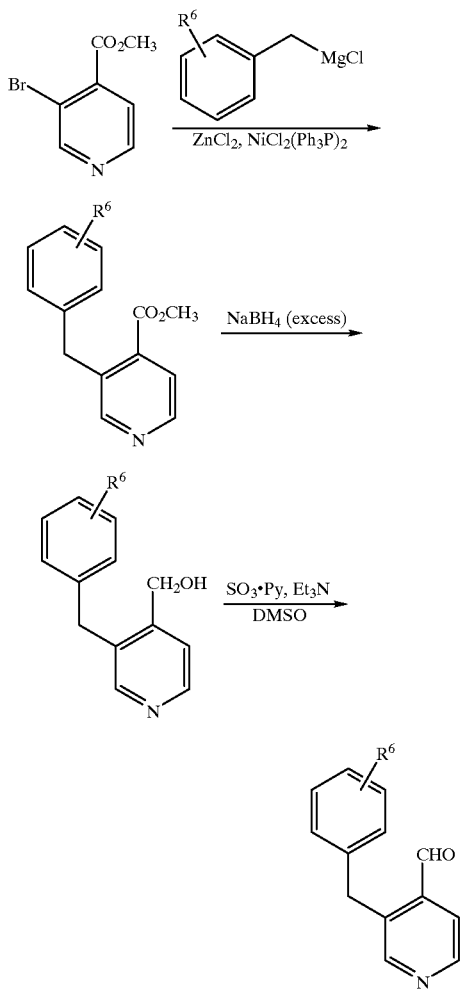

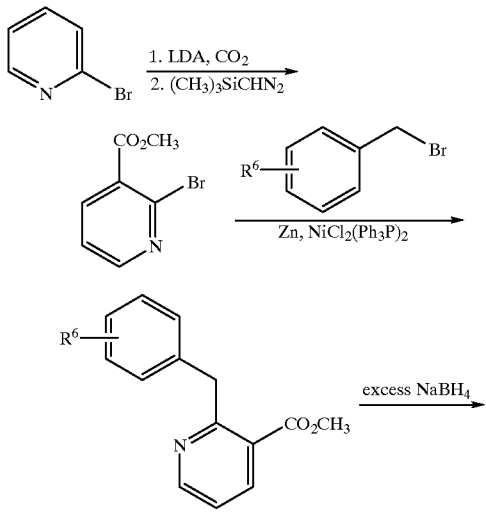

REACTION SCHEME 10

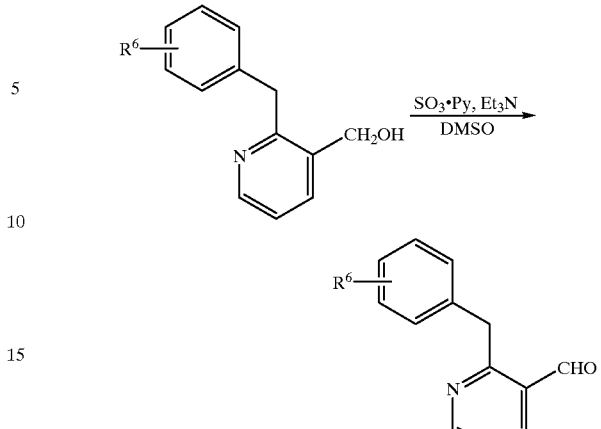

Such benzodiazepine analogs may be synthesized by techniques well known in the art. General methods of synthesis of the benzediazapine analogs of this invention are shown in Schemes 1,2 and 3. Typically a convergent route is employed, which joins the key intermediate 6 (Scheme 2) and $R^a$ and $R^b$ components (Schemes 2 and 3) using standard bond-forming procedures.

As shown in Scheme 1, the amine 6 may be prepared from a suitably substituted 2-aminobenzoketone (2). Many 2-aminobenzoketones are known in the art or are available form commercial sources such as Aldrich Chemical Co. General methods for the synthesis of new 2-aminobenzophenones (e.g Walsh, D. A. Synthesis, 677–688 (1980), Gates, M. J. Org. Chem 45, 1675, 1980,) and 2-aminobenzoketones may be found in the literature (e.g. Chambers, M. S, Bioorganic and Medicinal Chemistry, Vol 3, 1919 1993).

Acylation of 2 with an haloacetyl halide, followed by treatment with ammonia in methanol gives the 1,4-benzodiazepin-2-one 3. The amide 3 may be alkylated at N-1 with an appropriate alkyl halide in the presense of a base such as cesium carbonate to afford the amide 4.

The amide 4 can be converted to the amine 6 via a two step protocol. Electrophillic azidination of the enolate anion generated by treatment of 4 with strong base such as sodium hexamethyl disilazide, with triisopropylbenzenesulfonylazide. Reduction of the azide by treatment of 5 with triphenylphosphine in aqueous THF affords the amine 6. The amine 6 may be derivatized by acylation, reductive amination or alkylation to afford compounds of this invention (scheme 2). The syntheses of the required acylating, and alkylating reagents are shown in schemes 4, 5 and 6.

Syntheses of alternatively functionalized benzodiazepines are shown in scheme 3. Protection of the amide 3 with a 4-methoxy benzyl group allows the 3-amino group to be introduced efficiently. Subsequent deprotection of the amide and alkylation with a suitably protected bromoacetate for example methyl bromoacetate can afford compound 15. Hydrolysis of the ester and amide bond formation with the amine NH(R2)R3R5 can give the amide 17. For compounds where $R^b \neq H$, 17 (scheme 3) can be alkylated at N-3 with a wide variety of alkylating agents according to the standard procedure of Benoiton, et al., Can. J. Chem. 1977, 55, 906. to give 18. The amine 18 can be acylated or alkylated to afford compounds of this invention (for example 19).

Schemes 7–10 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, ab1, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of 3(R)-3-{[1-(4-Cyanobenzyl) imidazol-5-yl-methylamino]}-5-phenyl-1-(2,2,2-trifluoroethyl)-H-benzo[e][1,4]diazepine-2-one.

Step A: 1-Triphenylmethyl-4-(hydroxymethyl)-imidazole

To a solution of 4-(hydroxymethyl)imidazole hydrochloride (35.0 g, 260 mmol) in 250 mL of dry DMF at room temperature was added triethylamine (90.6 mL, 650 mmol). A solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a solid which was sufficiently pure for use in the next step.

Step B: 1-Triphenylmethyl-4-(acetoxymethyl)-imidazole

Alcohol from Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a powder which was sufficiently pure for use in the next reaction.

Step C: 1-(4-Cyanobenzyl)-5-(acetoxymethyl)-imidazole hydrobromide

A solution of the product from Step B (85.8 g, 225 mmol) and α-bromo-p-tolunitrile (50.1 g, 232 mmol) in 500 mL of EtOAc was stirred at 60° C. for 20 hours, during which a precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a solid. All of the solid material was combined, dissolved in 500 mL of methanol, and warned to 60° C. After two hours, the solution was reconcentrated in vacuo to provide a solid which was triturated with hexane to remove soluble materials. Removal of residual solvents in vacuo provided the titled product hydrobromide as a solid which was used in the next step without further purification.

Step D: 1-(4-Cyanobenzyl)-5-(hydroxymethyl)-imidazole

To a solution of the acetate from Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a solid which was sufficiently pure for use in the next step without further purification.

Step E: 1-(4-Cyanobenzyl)-5-imidazolecarboxaldehyde

To a solution of the alcohol from Step D (21.5 g, 101 mmol) in 500 mL of DMSO at room temperature was added triethylamine (56 mL, 402 mmol), then SO$_3$-pyridine complex (40.5 g, 254 mmol). After 45 minutes, the reaction was poured into 2.5 L of EtOAc, washed with water (4×1 L) and brine, dried (Na$_2$SO$_4$), filtered, and concentrated in vacuo to provide the aldehyde as a powder which was sufficiently pure for use without further purification.

Step F: 2,3-Dihydro-2-oxo-5-phenyl-1H-1,4-benzodiazepine[1]

To a stirring solution of 2-aminobenzophenone (50 g, 0.25 mole) in methylene chloride (1 L) was added bromoacetyl bromide (58.0 g, 0.25 mole). An ice water bath was applied to maintain reaction temperature at <30° C. Sodium hydroxide (250 mL of a 3 N solution) was then added over 10 minutes and the cooling bath removed. The reaction was stirred at ambient temperature for 1 hour and poured into a separatory funnel. The layers were separated and the aqueous phase was extracted with methylene chloride (300 mL). The combined organic layers were dried over anhydrous sodium sulfate, filtered and concentrated at reduced pressure. The resulting solid was suspended in ethanol (2 L), treated with concentrated ammonium hydroxide (1.5 L), and stirred at room temperature for two days. The reaction was concentrated at reduced pressure to remove most of the ethanol and extracted with methylene chloride (2×1 L). The combined organics were dried over anhydrous sodium sulfate, filtered and concentrated. The residue was triturated with ethyl ether and the solid collected and dried overnight in vacuo. MP. 179–180° C. $^1$H NMR CDCl$_3$, δ9.73 (br s, 1H), 7.65–7.10 (m, 9H), 4.35 (br s, 2H). 1. Bock, M. G.; Dipardo, R. M.; Evans, B. E.; Rittle, K. E.; Veber, D. F.; Freidinger, R. M. *J. Org. Chem.*, 1987, 52, 939–942.

Step G: 2,3-Dihydro-1-(2,2,2-trifluoroethyl)-2-oxo-5-phenyl-1H-1,4-benzodiazepine A solution of 5-phenyl-1,4-benzodiazepine-2-one (50 g, 0.211 mole) in DMF (100 mL) was treated with cesium carbonate (103.5 g, 0.317 mole) and trifluoroethyl iodide (109.7 g, 0.525 mole). The mixture was stirred at 50° C.–60° C. overnight. The reaction mixture was then poured into water (2 L) and extracted with ethyl acetate (3×1 L). The combined ethyl acetate fractions were dried over anhydrous magnesium sulfate, filtered and concentrated at reduced pressure. The material was chromatographed on silica gel (1.5 Kg) eluting with 1:1 ethyl acetate/heaxane. The combined pure fractions were concentrated at reduced pressure. The residue was swished with warm ethyl ether, cooled and filtered to give the product. MP=130–131° C.; $^1$H NMR CDCl$_3$, δ7.65–7.60 (m, 2H), 7.60–7.45 (m, 5H), 7.40–7.20 (m, 2H), 5.25 (dq, J=14, 8.6 Hz, 1H), 4.82(d, J=10.5 Hz, 1H), 4.15 (app sextet, J=8.6 Hz, 1H), 3.81 (d, J=10.5 Hz, 1H).

Step H: 3-Azido-5-phenyl-1-(2,2,2-trifluoroethyl)-1H-benzo[e][1,4]diazepine-2-one To a stirring solution of 5-phenyl-1-(2,2,2-trifluoroethyl)--H-benzo[e][1,4]diazepine-2-one (66 g, 0.209 mole) in THF (1200 mL) cooled to −78° C. was added potassium tert-butoxide (229 mL of a 1 N solution in THF dropwise over 30 min. A solution of the anion was obtained. A solution of 2,4,6-triisopropylbenzenesulfonylazide (71 g, 0.229 mole) in THF (200 mL) was added over 20 min. This was stirred for 10 min, acetic acid (50 g, 48 ml, 0.834 mole) was added and the reaction allowed to warm to ambient temperature over 4 hours. The reaction was poured into sat. NaHCO$_3$ (1L) and extracted with ethyl acetate (2×500 mL). The organic layers were combined, washed once with water then brine, dried with Na$_2$SO$_4$ and evaporated at reduced pressure. The residue was dissolved in THF (500 mL) and then filtered to give a solid which was discarded. The solution of crude azide was used without further purification.

$^1$H NMR CDCl$_3$, δ7.70–7.26 (m,9H), 5.28–5.12 (m,1H), 4.63 (s,1H), 4.35–4.10 (m,1H).

Step I: 3-Amino-5-phenyl-1-(2,2,2-trifluoroethyl)-1H-benzo[e][1,4]diazepine-2-one To a stirring solution of 3-azido-5-phenyl-1-(2,2,2-trifluoroethyl)-1H-benzo[e][1,4]diazepine-2-one (crude from above) in 1.3 L THF was added triphenylphosphine (109 g, 0.417 mol) and water (150 mL). This was stirred overnight at ambient temperature The reaction was then concentrated under reduced pressure, taken up in 1N HCl (1500 mL), and extracted with ethyl ether (2×500 mL). The combined organics were back extracted with 1N HCl (1×300 mL). The combined aqueous layers were back extracted with ethyl acetate (100 mL) and then basefied with sat. NaHCO$_3$ (100 mL) and 50% NaOH until pH=10. This was extracted with ethyl acetate (2×500 mL). The combined ethyl acetate fractions were dried over Na$_2$SO$_4$, evaporated under reduced pressure and crystallized from ethyl ether to give the title compound as a powder. MP=141–143° C.;

$^1$H NMR CDCl$_3$, δ7.70–7.26 (m,9H), 5.28–5.12 (m,1H), 4.57 (s,1H), 4.35–4.10 (m,1H).

Step J: 2-(R)-2-amino-N-[3R-2-oxo-5-phenyl-1-(2,2,2-trifluoroethyl)-2,3-dihydro-1H-benzo[e][1,4]diazepin-3-yl]-3-phenyl-propionamide and 2-(R)-2-amino-N-[3(S)-2-oxo-5-phenyl-1-(2,2,2-trifluoroethyl)-2,3-dihydro-1H-benzo[e][1,4]diazepin-3-yl]-3-phenyl-propionamide To a mixture of 3-amino-5-phenyl-1-(2,2,2-trifluoroethyl)-1H-benzo[e][1,4]diazepine-2-one (20.0 g, 60.3 mmol), Boc-D-phenylalanine (17.6 g, 66.3 mmol), 1-(3-dimethylaminopropyl)-3-ethylcarbodiimide hydrochloride. (15.0 g, 78.4 mmol), and 1-hydroxybenztriazole hydrate (10.6 g, 78.4 mmol) was added DMF (200 mL). This was stirred at ambient temperature for 2 h. The reaction was diluted with sat. NaHCO$_3$ (1 L) and extracted with ethyl acetate(2×400 mL.) The combined organics were washed with 10% KHSO$_4$ (1×400 mL), dried over Na$_2$SO$_4$, and evaporated to a foam. (40.91 g, >100%, contains residual ethyl acetate). This material was carried on without purification.

To a stirred solution of 2-(tert-butoxycarbonylamino)-N-[2-oxo-5-phenyl-1-(2,2,2-trifluoroethyl)-2,3-dihydro-1H-benzo[e][1,4]diazepin-3-yl]-3-phenylpropionamide in ethyl acetate (300 mL) cooled with an ice bath was bubbled HCl gas for 1 h. The reaction temperature was kept below 10° C.

The reaction was evaporated under reduced pressure, the residue taken up in ice cold sat. NaHCO$_3$ (700 mL) and ethyl acetate. (500 mL) The phases were separated and the aqueous extracted with ethyl acetate. (1×500 mL). The organic layers were combined, dried over Na$_2$SO$_4$ and evaporated under reduced pressure. This was chromatographed over a 10×50 cm. silica column, eluted with 1% methanol:ethyl acetate. The upper R$_f$ spot was isolated and evaporated under reduced pressure to give the 2R,3R diastereomer as a solid. The lower R$_f$ spot was isolated and evaporated under reduced pressure to give the 2(R),(3S) diastereomer as a solid.

$^1$H NMR CDCl$_3$, δ8.94 (d, J=8.6Hz, 1H), 7.65–7.10 (m, 9H), 5.64 (d, J=8.6 Hz, 1H), 5.28–5.12 (m, 1H), 4.57 (s, 1H), 4.35–4.10 (m, 1H) 3.71 (dd, J=9.8 and 3.9 Hz, 1H), 3.34 (dd, J=13.9 and 3.9 Hz,1H), 2.79 (dd, J=13.9 and 10.0 Hz, 1H).

Step K: 3-(R)-(+)-3-amino-5-phenyl-1-(2,2,2-trifluoroethyl)-H-benzo[e][1,4]diazepine 2-one To a stirring solution of 2-(R)-2-amino-N-[3R-2-oxo-5-phenyl-1-(2,2,2-trifluoroethyl)-2,3-dihydro-1H-benzo[e][1,4]diazepin-3-yl]-3-phenyl-propionamide (13.6 g, 28.3 mmol) in methylene chloride (136 ml) was added phenyl isothiocynate (3.87 mL, 32.3 mmol). This was stirred overnight at ambient temperature. The reaction was cooled in ice, trifluoroacetic acid (27 mL, 0.283 mol) was added and the reaction allowed to warm to ambient temperature. After stirring at ambient temperature for 2.5 hours the reaction was evaporated under reduced pressure, chromatographed on silica gel (500 g) eluting with with 90:10:1:1 methylene chloride:methanol:acetic acid:water. The low R$_f$ spot was collected and evaporated under reduced pressure with no heat. The residue was taken up in 600 mL methylene chloride and washed with 300 mL sat. NaHCO$_3$, 300 mL water, dried over Na$_2$SO$_4$, evaporated under reduced pressure, and crystallized from ethyl acetate/hexanes to give 6.65 g of a powder. [α]D=+72.9° (c=0.7, MeOH), MP=156–158° C.;

$^1$H NMR CDCl$_3$, δ7.70–7.26 (m,9H), 5.28–5.12 (m,1H), 4.57 (s,1H), 4.35–4.10 (m,1H).

Step L: 3S-(+)-3-Amino-5-phenyl-1-(2,2,2-trifluoro-ethyl)-H-benzo[e][1,4]diazepine 2-one The title compound was prepared using the procedure decribed in step F using 2(R)-2-amino-N-[3(S)-2-oxo-5-phenyl-1-(2,2,2-trifluoroethyl)-2,3-dihydro-1H-benzo[e][1,4]diazepin-3-yl]-3-phenyl-propionamide.

Step M: 3(R)-3-{1-(4-Cyanobenzyl)imidazol-5-yl-methylamino}-5-phenyl-1-(2,2,2-trifluoroetbyl)-H-benzor[e][1,4]diazepine-2-one To a mixture of 3(R)-(+)-3-amino-5-phenyl-1-(2,2,2-trifluoroethyl)-H -benzo[e][1,4]diazepine-2-one (from stepK) (99.8 mg, 0.299 mmol) the aldehyde (from example 1, step E) (79.5 mg, 0.376 mmol) and 3A molecular sieves (324 mg) in methanol (3 ml) was added sodium cyanoborohydride (0.375 ml of a 1M solution in THF, 0.375 mmol). The pH was adjusted to 5 by addition of acetic acid and the reaction stirred under argon for 48 h at room temperature. The solids were removed by filtration and the filtrate partitioned between EtOAc and sat. NaHCO$_3$ solution, the organic extracts were dried (MgSO$_4$) and the solvent evaporated in vacuo. The residue was purified by preparative HPLC (C-18, gradient elution, 95:5 to 5:95 Water:acetonitrile containing 0.1% trifluoroacetic acid). Lyophilization afforded the title compound as a powder.

Anal. Calcd for C$_{29}$H$_{23}$N$_6$OF$_{3.2.40}$ TFA.0.30H$_2$O: C, 50.27; H, 3.25; N, 10.41. Found: C, 50.28; H, 3.23; N, 10.54.

FAB HRMS exact mass calcd for C$_{29}$H$_{24}$N$_6$OF$_3$: 529.196369 MH$^+$); found 529.196770.

$^1$H NMR CD$_3$OD δ8.91 (1H, d, J=1.5 Hz), 7.90–7.30 (14H, m), 5.73(2H, s), 5.20(1H,m), 4.66(1H, s), 4.60(1H, m), 4.24(1H, d, J=5.0 Hz) and 4.10(1H, d, J=5.0 Hz) ppm.

Example 2

Preparation of 3(S)-3-{1-(4-Cyanobenzyl)imidazol-5-yl-methylamino-}-5-phenyl-1-(2,2,2-trifluoroethyl)-H-benzo[e][1,4]diazepine 2-one.

To a mixture of 3S-(+)-3-amino-5-phenyl-1-(2,2,2-trifluoroethyl)-H-benzo[e][1,4]diazepine-2-one (from step L) (99.8 mg, 0.299 mmol), the aldehyde (from Example 1, step E) (81.5 mg, 0.386 mmol) and 3A molecular sieves (324 mg) in methanol (3 ml) was added sodium cyanoborohydride (0.375 ml of a 1M solution in THF, 0.375 mmol). The pH was adjusted to 5 by addition of acetic acid and the reaction stirred under argon for 48 h at room temperature. The solids were removed by filtration and the filtrate partitioned between EtOAc and sat. NaHCO$_3$ solution; the organic extracts were dried (MgSO$_4$) and the solvent evaporated in vacuo. The residue was purified by preparative HPLC (C-18, gradient elution, 95:5 to 5:95 Water:acetonitrile containing 0.1% trifluoroacetic acid). Lyophilization afforded the title compound as a powder.

Anal. Calcd for C$_{29}$H$_{23}$N$_6$OF$_3$.2.30 TFA.0.30H$_2$O: C, 50.69; H, 3.28; N, 10.56. Found: C, 50.70; H, 3.26; N, 10.66.

FAB HRMS exact mass calcd for C$_{29}$H$_{24}$N$_6$OF$_3$: 529.196369 MH$^+$); found 529.195981.

$^1$H NMR CD$_3$OD δ8.91 (1H, d, J=1.5 Hz), 7.90–7.30 (14H, m), 5.73(2H, s), 5.19(1H,m), 4.65(1H, s), 4.60(1H, m), 4.24(1H, d, J=5.0 Hz) and 4.10(1H, d, J=5.0 Hz) ppm.

Example 3

Preparation of 3(R)-3-[1-(4-Cyanobenzyl)imidazol-5-yl-acetylamino]}-5-phenyl-1-(2,2,2-trifluoroethyl)-H-benzo[e][1,4]diazepine 2-one Step A: 1H-Imidazole-4-acetic acid methyl ester hydrochloride A solution of 1H-imidazole-4-acetic acid hydrochloride (4.00 g, 24.6 mmol) in methanol (100 ml) was saturated with gaseous hydrogen chloride. The resulting solution was allowed to stand at room temperature (RT) for 18 hr. The solvent was evaporated in vacuo to afford the title compound as a solid.

$^1$H NMR CDCl$_3$, δ8.85(1H,s), 7.45(1H,s), 3.89(2H,s) and 3.75(3H,s) ppm.

Step B: 1-(Triphenylmethyl)-1H-imidazol-4-ylacetic acid methyl ester

To a solution of the product from Step A (24.85 g, 0.141 mol) in dimethylformamide (DMF) (15 ml) was added triethylamine (57.2 ml, 0.412 mol) and triphenylmethyl bromide(55.3 g, 0.171 mol) and the suspension was stirred for 24 hr. After this time, the reaction mixture was diluted with EtOAc (1 l) and water (350 ml). The organic phase was washed with sat. aq. NaHCO$_3$ (350 ml), dried (Na$_2$SO$_4$) and evaporated in vacuo. The residue was purified by flash chromatography (SiO$_2$, 0–100% ethyl acetate in hexanes; gradient elution) to provide the title compound as a solid.

$^1$H NMR CDCl$_3$, δ7.35(1H, s), 7.31(9H,m), 7.22(6H,m), 6.76(1H, s), 3.68(3H, s) and 3.60(2H, s) ppm.

Step C: [1-(4-cyanobenzyl)-1H-imidazol-5-yl]acetic acid methyl ester

To a solution of the product from Step B (8.00 g, 20.9 mmol) in acetonitrile (70 ml) was added bromo-p-toluonitrile (4.10 g, 20.92 mmol) and heated at 55° C. for 3 hr. After this time, the reaction was cooled to room temperature and the resulting imidazolium salt (white precipitate) was collected by filtration. The filtrate was heated at 55° C. for 18 hr. The reaction mixture was cooled to room temperature and evaporated in vacuo. To the residue was added EtOAc (70 ml) and the resulting precipitate collected by filtration. The precipitated imidazolium salts were combined, suspended in methanol (100 ml) and heated to reflux for 30 min. After this time, the solvent was removed in vacuo, the resulting residue was suspended in EtOAc (75 ml) and the solid isolated by filtration and washed (EtOAc). The solid was treated with sat. aq. NaHCO$_3$ (300 ml) and CH$_2$Cl$_2$ (300 ml) and stirred at room temperature for 2 hr. The organic layer was separated, dried (MgSO$_4$) and evaporated in vacuo to afford the title compound as a solid.

$^1$HNMR CDCl$_3$, δ7.65(1H, d, J=8.0 Hz), 7.53(1H, s), 7.15(1H, d, J=8.0 Hz), 7.04(1H, s), 5.24(2H, s), 3.62(3H, s) and 3.45(2H, s) ppm.

Step D: [1-(4-Cyanobenzyl)-1H-imidazol-5-yl]acetic acid

A solution of [1-(4-cyanobenzyl)-1H-imidazol-5-yl] acetic acid methyl ester (4.44 g, 17.4 mmol) in THF (100 ml) and 1 M lithium hydroxide (17.4 ml, 17.4 mmol) was stirred at room temperature for 18 hr. 1 M HCl (17.4 ml) was added and the THF was removed by evaporation in vacuo. The aqueous solution was lyophilized to afford the title compound containing lithium chloride as a solid.

$^1$H NMR CD$_3$OD, δ8.22(1H, s), 7.74(1H, d, J=8.4 Hz), 7.36(1H, d, J=8.4 Hz), 7.15(1H, s), 5.43(2H, s) and 3.49(2H, s) ppm.

Step E: 3(R)-3-{1-(4-Cyanobenzyl)imidazol-5-yl-acetylamino}-5-phenyl-1-(2,2,2-trifluoroethyl)-H-benzo[e][1,4]diazepine 2-one To a mixture of 3(R)-(+)-3-amino-5-phenyl-1-(2,2,2-trifluoroethyl)-H-benzo[e][1,4]diazepine 2-one (from example 1, step K) (100.5 mg, 0.302 mmol), [1-(4-cyanobenzyl)-1H-imidazol-5-yl]acetic acid (from step D) (85.9 mg, 0.303 mmol), HOOBT (60.4 mg, 0.37 mmol) and triethylamine (0.10 ml, 0.717 mmol) in DMF (3 ml) was added EDC (71 mg, 0.37 mmol) and the reaction was stirred at room temperature for 24 h. The reaction was diluted with EtOAc (50 ml) and washed with sat. NaHCO$_3$ solution; the organic extracts were dried (Na$_2$SO$_4$) and the solvent evaporated in vacuo. The residue was purified by preparative HPLC (C-18, gradient elution, 95:5 to 5:95 Water:acetonitrile containing 0.1% trifluoroacetic acid). Lyophilization afforded the title compound as a powder.

Anal. Calcd for C$_{32}$H$_{23}$N$_6$O$_2$F$_3$.1.60 TFA: C, 53.96 H, 3.36; N, 11.37. Found: C, 54.02 H, 3.36; N, 11.18.

FAB MS 557 (MH$^+$).

$^1$H NMR CD$_3$OD δ9.01 (1H, d, J=1.5Hz), 7.90–7.30 (14H, m), 5.60 (2H, s), 5.35(1H,m), 5.20(1H, m), 4.60(1H, m) and 3.86(2H,m) ppm.

Example 4

Preparation of 3(S)-3-[1-(4-Cyanobenzyl)imidazol-5-yl-acetylamino-]-5-phenyl-1-(2,2,2-trifluoroethyl)-H-benzo[e][1,4]diazepine 2-one To a mixture of 3S-(+)-3-amino-5-phenyl-1-(2,2,2-trifluoroethyl)-H-benzo[e][1,4]diazepine 2-one (from example 1, step L) (46.3 mg, 0.139 mmol), [1-(4-cyanobenzyl)-1H-imidazol-5-yl]acetic acid (from example 5, step D) (39.4 mg, 0.139 mmol), HOOBT (29.1 mg, 0.178 mmol) and triethylamine (0.05 ml, 0.36 mmol) in DMF (1.4 ml) was added EDC (32 mg, 0.17 mmol) and the reaction stirred at room temperature for 24 h. The reaction was diluted with EtOAc (50 ml) and washed with saturated NaHCO$_3$ solution, the organic extracts were dried (Na$_2$SO$_4$)

and the solvent evaporated in vacuo. The residue was purified by preparative HPLC (C-18, gradient elution, 95:5 to 5:95 Water:acetonitrile containing 0.1% trifluoroacetic acid). Lyophilization afforded the title compound as a powder.

Anal. Calcd for $C_{32}H_{23}N_6O_2F_3$.1.50 TFA: C, 54.48H, 3.39 N, 11.55. Found: C, 54.49 H, 3.32; N, 11.42.

FAB MS 557 (MH$^+$).

$^1$H NMR CD$_3$OD δ9.01 (1H, d, J=1.5 Hz), 7.90–7.30 (14H, m), 5.60(2H, s), 5.36(1H,m), 5.21(1H, m), 4.61(1H, m) and 3.86(2H,m) ppm.

Example 5

Preparation of 3(R,S)-3-[1-(4-Cyanobenzyl) imidazol-5-yl-acetylamino-]-5-phenyl-1-(4-methoxy benzyl)-H-benzo[e][1,4]diazepine 2-one To a mixture of 3(R,S)-amino-5-phenyl-1-(4 methoxybenzyl)-H-benzo[e][1,4]diazepine 2-one (prepared as in example 1, steps F-I using 4-methoxybenzyl bromide in place of trifluoroethyl iodide and potassium carbonate as base) (100 mg, 0.269 mmol), [1-(4-cyanobenzyl)-1H-imidazol-5-yl]acetic acid (from example 3 step D) (76.6 mg, 0.270 mmol), HOOBT (55.2 mg, 0.338 mmol) and triethylamine (0.090 ml, 0.65 mmol) in DMF (3.0 ml) was added EDC (63 mg, 0.33 mmol) and the reaction stirred at room temperature for 24 h. The reaction was diluted with EtOAc (50 ml) and washed with saturated NaHCO$_3$ solution; the organic extracts were dried (Na$_2$SO$_4$) and the solvent evaporated in vacuo. The residue was purified by preparative HPLC (C-18, gradient elution, 95:5 to 5:95 Water:acetonitrile containing 0.1% trifluoroacetic acid). Lyophilization afforded the title compound as a powder.

Anal. Calcd for $C_{38}H_{30}N_6O_3$.1.80 TFA, 0.15H$_2$O: C, 59.26H, 4.03 N, 10.47. Found: C, 59.27 H, 4.01; N, 10.31.

$^1$H NMR CD$_3$OD δ9.02 (1H, s), 7.80–7.10(14H, m), 6.91(2H,d, J=9.7 Hz), 6.62(2H, d, J=9.7 Hz), 5.70–5.50(4H, m), 5.31(1H,s), 3.90(2H,m), and 3.68(3H,s) ppm.

Example 6

Preparation of 3(R)-3-[1-(4-Cyanobenzyl)imidazol-5-yl-acetylamino-]-5-phenyl-1-(methyl)-H-benzo[e][1,4]diazepine 2-one To a mixture of 3(R)-amino-5-phenyl-1-(methyl)-H-benzo[e][1,4]diazepine-2-one (prepared as in example 1, steps F-I using methyl iodide in place of trifluoroethyl iodide) (99.8 mg, 0.376 mmol), [1-(4-cyanobenzyl)-1H-imidazol-5-yl]acetic acid (from example 3, step D) (110.0 mg, 0.388 mmol), HOOBT (74.4 mg, 0.338 mmol) and triethylamine (0.125 ml, 0.897 mmol) in DMF (4.0 ml), was added EDC (63 mg, 0.33 mmol) and the reaction was stirred at room temperature for 24 h. The reaction was diluted with EtOAc (50 ml) and washed with saturated NaHCO$_3$ solution; the organic extracts were dried (Na$_2$SO$_4$) and the solvent evaporated in vacuo. The residue was purified by preparative HPLC (C-18, gradient elution, 95:5 to 5:95 Water:acetonitrile containing 0.1% trifluoroacetic acid). Lyophilization afforded the title compound as a powder.

Anal. Calcd for $C_{29}H_{24}N_6O_3$.1.95TFA, 0.70H$_2$O: C, 54.62H, 3.81 N, 11.62. Found: C, 54.64 H, 3.57; N, 11.47.

FAB MS 489 (MH$^+$).

$^1$H NMR CD$_3$OD δ9.02 (1H, d, J=1.7 Hz), 7.80–7.30 (14H, m), 5.61(2H,s), 5.24(1H,s), 3.90(1H, d, J=17.4 Hz), 3.85(1H, d, J=17.4 Hz), and 3.50(3H,s) ppm.

Example 7

Preparation of 3(R)-3-[1-(4-Cyanobenzyl)imidazol-5-yl-acetylamino-]-5-(4-fluorophenyl-1-(2,2,2 trifluoroethyl)-H-benzo[e][1,4]diazepine-2-one To a mixture of 3(R)-amino-5-(4-fluorophenyl)-1-(2,2,2-trifluoroethyl)-H-benzo[e][1,4]diazepine-2-one (prepared as in example 1, steps E-I using 2-amino-4-'fluorobenzophenone in place of 2-aminobenzophenone), (100.1 mg, 0.285 mmol), [1-(4-cyanobenzyl)-1H-imidazol-5-yl]acetic acid (from example 3, step D) (80.9 mg, 0.285 mmol), HOOBT (58 mg, 0.36 mmol) and triethylamine (0.095 ml, 0.68 mmol) in DMF (3.0 ml) was added EDC (66 mg, 0.34 mmol), and the reaction stirred at room temperature for 24 h. The reaction was diluted with EtOAc (50ml) and washed with saturated NaHCO$_3$ solution; the organic extracts were dried (Na$_2$SO$_4$) and the solvent evaporated in vacuo. The residue was purified by preparative HPLC (C-18, gradient elution, 95:5 to 5:95 Water:acetonitrile containing 0.1% trifluoroacetic acid). Lyophilization afforded the title compound as a powder.

Anal. Calcd for $C_{30}H_{22}N_6O_3F_4$.1.50TFA, 0.15H$_2$O: C, 52.97 H, 3.21 N, 11.23. Found: C, 52.96 H, 3.01; N, 11.22.

FAB MS 575 (MH$^+$).

$^1$H NMR CD$_3$OD δ9.02 (1H, d, J=1.5 Hz), 7.80–7.10 (13H, m), 5.59(2H, s), 5.34(1H,s), 5.20(1H,m), 4.59(1H,m), 3.89(1H, d, J=17.3 Hz) and 3.82(1H, d, J=17.3 Hz) ppm.

Example 8

Preparation of 3-[5-Oxo-pyrrolidine-2(S)-carbonylamino]-2,3-dihydro-2-oxo-5-phenyl-1H -1, 4-benzodiazepine A solution of 3-amino-2,3-dihydro-2-oxo-5-phenyl-1H-1,4-benzodiazepine hydrogen bromide (142 mg, 0.426 mmol), prepared by sequential treatment of an aqueous acetonitrile solution of the 4-methoxybenzyl derivative from example 5 with ammonium cerium IV nitrate, potassium tartrate solution and HBr/acetic acid-(L)-pyroglutamic acid (60.2 mg, 0.466 mmol), EDC (91 mg, 0.473 mmol), HOBT (63.5 mg, 0.473 mmol), and diisopropylethylamine (0.082 ml, 0.473 mmol) in DMF (5 ml) was stirred at room temperature for 18 hours. The resultant solution was concentrated in vacuo, and the residue partitioned between ethyl acetate and aqueous sodium bicarbonate solution. The organic extract was washed with brine, dried, (MgSO$_4$), filtered, and concentrated. The residue was purified by preparative HPLC (C18, eluted with a 5:95 to 40:60 water:acetonitrile). Lyophilization provided the titled compound as a 1:1 mixture of diastereomers.

$^1$H NMR DMSO δ10.9 (two singlets, 1H), 9.21 (two doublets, 1H), 7.95 (two singlets, 1H), 7.7–7.2 (m, 9H), 5,24 (m, 1H), 4.31 (m, 1H);

FAB MS 363 (MH$^+$);

Anal. Calcd for $C_{20}H_{18}N_4O_3$.0.19 CF$_3$COOH.0.37 H$_2$O: C, 62.65; H, 4.88; N, 14.34. Found: C, 62.66; H, 4.87; N, 14.59.

Example 9

Preparation of 3(R)-3-[1-(4-Cyanobenzyl)imidazol-5-yl-ethylamino-]-5-phenyl-1-(2,2,2-trifluoroethyl)-H-benzo[e][1,4]diazepine-2-one Step A: Preparation of 5-[1-(4-Cyanobenzyl)-1H-imidazolyl]ethanol To a stirred solution of the ester from example 3, step C, (1.50 g, 5.88 mmol), in methanol (20 ml) at 0° C., was added sodium borohydride (1.0 g, 26.3 mmol) portionwise over 5 minutes. The reaction was stirred at 0° C. for 1 hr and then at room temperature for an additional 1 hr. The reaction was quenched by the addition of sat.NH4Cl solution and the methanol evaporated in vacuo. The residue was partitioned between EtOAc and sat NaHCO$_3$ solution and the organic extracts dried (MgSO$_4$) and evaporated in vacuo. The residue was purified by chromatography (SiO$_2$, gradient elution 4 to 10% methanol in methylene chloride) to afford the title compound as a solid.

$^1$H NMR CDCl$_3$ δ7.64(2H, d, J=8.2 Hz), 7.57(1H, s), 7.11(2H, d, J=8.2 Hz), 6.97(1H,s), 5.23(2H, s), 3.79(2H, t, J=6.2 Hz), 2.66(2H, t, J=6.2 Hz) ppm.

Step B: 5-(-1-(4-Cyanobenzyl)-imidazolyl)ethyl methanesulfonate

A solution of 5-[1-(4-cyanobenzyl)-1H-imidazolyl] ethanol (0.500 g, 2.20 mmol) in methylene chloride (6 ml) at 0° C. was treated with Hunig's base (0.460 ml, 2.64 mmol) and methane sulfonyl chloride (0.204 ml, 2.64 mmol). After 2 hours, the reaction was quenched by addition of saturated NaHCO$_3$ solution (50 ml) and the mixture was extracted with methylene chloride (50 ml), dried MgSO$_4$ and the solvent was evaporated in vacuo. The title compound was used without furthur purification.

$^1$H NMR CDCl$_3$δ7.69 (1H, s) 7.66(2H, d, J=8.2 Hz), 7.15 (2H, d,J=8.2 Hz), 7.04(1H, s), 5.24(2H, s), 4.31(2H, t, J=6.7 Hz), 2.96(3H, s), and 2.88(2H, t, J=6.6 Hz)ppm.

Step C: 3(R)-3-[1-(4-Cyanobenzyl)imidazol-5-yl-ethylamino-]-5-phenyl-1-(2,2,2-trifluoroethyl)-H-benzo[e] [1,4]diazepine-2-one A mixture of 3R-(+)-3-amino-5-phenyl-1-(2,2,2-trifluoroethyl)-H-benzo[e][1,4]diazepine-2-one (from example 1, step K) (99.5 mg, 0.299 mmol), 5-(-1-(4-Cyanobenzyl)-imidazolyl)ethyl methanesulfonate (from step B) (94.5 mg, 0.309 mmol), K$_2$CO$_3$ (108 mg, 0.781 mmol) and sodium iodide (185 mg, 1.23 mmol) in DMF (1.5 ml) was stirred under argon at 55° C. for 24 h. Additional mesylate (93 mg 0.30 mmol) was added and heating continued for 24 h. The reaction mixture was partitioned between EtOAc and saturated NaHCO$_3$ solution, the organic extracts were dried (MgSO$_4$) and the solvent evaporated in vacuo. The residue was purified by preparative HPLC (C-18, gradient elution, 95:5 to 5:95 Water:acetonitrile containing 0.1% trifluoroacetic acid). Furthur purification by flash chromatography, (SiO$_2$ eluting with 2.5% NH$_4$OH in acetonitrile), conversion to the corresponding hydrochloride salt with gaseous HCl in EtOAc and evaporation of the solvent in vacuo afforded the title compound as a powder.

Anal. Calcd for C$_{30}$H$_{25}$N$_6$OF$_3$.2.0HCl.1.20H$_2$O: C, 56.56 H, 4.65; N, 13.19. Found: C, 56.54; H, 4.78; N, 12.93.

FAB HRMS exact mass calcd for C$_{30}$H$_{26}$N$_6$OF$_3$: 543.212019MH$^+$); found 543.212383.

$^1$H NMR CD$_3$OD δ9.07 (1H, s), 7.90–7.30(14H, m), 5.63(2H, s), 5.30–5.15(2H,m), 4.69(1H, m), 3.62(1H, dt, J=12.5 and 7.9 Hz), 3.47–3.38(1H, m) and 3.14(2H,t, J=7.9 Hz) ppm.

Example 10

Preparation of 3(S)-3-[1-(4-Cyanobenzyl)imidazol-5-yl-ethylamino-]-5-phenyl-1-(2,2,2-trifluoroethyl)-H-benzo[e][1,4]diazepine-2-one A mixture of 3S-(+)-3-amino-5-phenyl-1-(2,2,2-trifluoroethyl)-H-benzo[e][1,4]diazepine-2-one (from example 1, step L), (102.5 mg, 0.307 mmol) 5-(-1-(4-Cyanobenzyl)-imidazolyl)ethyl methanesulfonate (from example 9, step B ) (93.0 mg, 0.305 mmol), K$_2$CO$_3$ (107 mg, 0.774 mmol) and sodium iodide (184 mg, 1.23 mmol) in DMF (1.5 ml) was stirred under argon at 55° C. for 24 h. Additional mesylate (93 mg 0.30 mmol) was added and heating continued for 24 h. The reaction mixture was partitioned between EtOAc and saturated NaHCO$_3$ solution; the organic extracts were dried (MgSO$_4$) and the solvent evaporated in vacuo. The residue was purified by preparative HPLC (C-18, gradient elution, 95:5 to 5:95 water:acetonitrile containing 0.1% trifluoroacetic acid). Furthur purification by flash chromatography, (SiO$_2$ eluting with 2.5% NH$_4$OH in acetonitrile), conversion to the corresponding hydrochloride salt with gaseous HCl in EtOAc and evaporation of the solvent in vacuo afforded the title compound as a powder.

Anal. Calcd for C$_{30}$H$_{25}$N$_6$OF$_3$.2.20HCl.1.20H$_2$O: C, 55.92 H, 4.63; N, 13.04. Found: C, 55.93; H, 4.63; N, 12.54.

FAB HRMS exact mass calcd for C$_{30}$H$_{26}$N$_6$OF$_3$: 543.212019MH$^+$); found 543.212542.

$^1$H NMR CD$_3$OD δ9.08 (1H, d, J=1.3 Hz), 7.90–7.30 (14H, m), 5.64(2H, s), 5.30–5.15(2H,m), 4.69(1H, m), 3.62 (1H, dt, J=12.5 and 7.9 Hz), 3.47–3.38(1H, m) and 3.15(2H, t, J=7.9 Hz) ppm.

Example 11

In vitro inhibition of ras farnesyl transferase

Assays of farnesyl-protein transferase

Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0 M HCL in ethanol. Precipitates were collected onto filter-mats. using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in Examples 1–10 were tested for inhibitory activity against human FPTase by the assay described above and were found to have IC$_{50}$ of <100 μM.

Example 12

In vivo ras farnesylation Assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1% /SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 13
In Vivo Growth Inhibition Assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound of the formula I

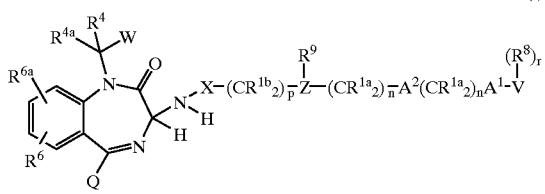

wherein $R^{1a}$ and $R^{1b}$ are independently selected from:
a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, NO$_2$, $(R^{10})_2N$—C(NR$^{10}$)—, $R^{10}C(O)$—, $R^{10}OC(O)$—, N$_3$, —N(R$^{10}$)$_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—C(NR$^{10}$)—, $R^{10}C(O)$—, $R^{10}OC(O)$—, N$_3$, —N(R$^{10}$)$_2$, and $R^{11}OC(O)$—NR$^{10}$—;

$R^4$ and $R^{4a}$ are independently selected from:
a) hydrogen,
b) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—C(NR$^{10}$)—, $R^{10}C(O)$—, $R^{10}OC(O)$—, N$_3$, —N(R$^{10}$)$_2$, and $R^{11}OC(O)$—NR$^{10}$—;

$R^6$ and $R^{6a}$ are independently selected from:
a) hydrogen,
b) halogen,
c) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—C(NR$^{10}$)—, $R^{10}C(O)$—, $R^{10}OC(O)$—, N$_3$, —N(R$^{10}$)$_2$, and $R^{11}OC(O)$—NR$^{10}$—;

$R^8$ is selected from:
a) hydrogen,
b) aryl, heterocycle, cycloalkyl, alkenyl, alkynyl, perfluoroalkyl, F, Cl, Br, $R^{10}O$—, $R^{11}S(O)_m$—, $R^{10}C(O)NR^{10}$—, CN, NO$_2$, $R^{10}{}_2N$—C(NR$^{10}$)—, $R^{10}C(O)$—, $R^{10}OC(O)$—, N$_3$, —N(R$^{10}$)$_2$, or $R^{11}OC(O)NR^{10}$—, and
c) $C_1$–$C_6$ alkyl unsubstituted or substituted by aryl, heterocycle, cycloalkyl, alkenyl, alkynyl, perfluoroalkyl, F, Cl, Br, $R^{10}O$—, $R^{11}S(O)_m$—, $R^{10}C(O)NH$—, CN, H$_2$N—C(NH)—, $R^{10}C(O)$—, $R^{10}OC(O)$—, N$_3$, —N(R$^{10}$)$_2$, or $R^{10}OC(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, NO$_2$, $(R^{10})_2N$—C(NR$^{10}$)—, $R^{10}C(O)$—, $R^{10}OC(O)$—, N$_3$, —N(R$^{10}$)$_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—C(NR$^{10}$)—, $R^{10}C(O)$—, $R^{10}OC(O)$—, N$_3$, —N(R$^{10}$)$_2$, or $R^{11}OC(O)NR^{10}$—;

$R^{10}$ is selected from hydrogen, $C_1$–$C_6$ alkyl, benzyl and aryl;

$R^{11}$ is selected from $C_1$–$C_6$ alkyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

Q is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, halogen $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

V is selected from:
 a) heterocycle,
 b) aryl;

W is selected from:
 a) hydrogen, or
 b) $CF_3$;

X is —$CH_2$—, —$C(=O)$—, or —$S(=O)_m$—;

Z is a heterocycle, selected from imidazolyl, pyrrolidinyl, pyridinyl, pyridonyl, 2-oxopiperidinyl, quinolinyl or isoquinolinyl;

m is 0, 1 or 2;

n is 0, 1, 2, 3 or 4;

p is 0, 1, 2, 3 or 4; and r is 1 to 5;

or the pharmaceutically acceptable salts thereof.

2. The compounds, according to claim 1, of formula I,

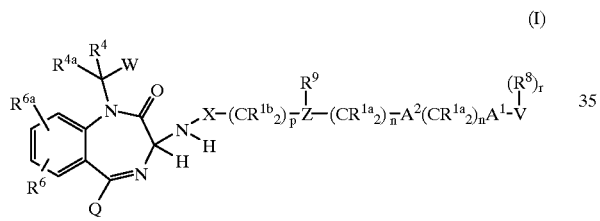

(I)

wherein $R^{1a}$ and $R^{1b}$ are independently selected from:
 a) hydrogen,
 b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
 c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^4$ and $R^{4a}$ are independently selected from:
 a) hydrogen,
 b) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^6$ and $R^{6a}$ are independently selected from:
 a) hydrogen,
 b) halogen,
 c) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^8$ is selected from:
 a) hydrogen,
 b) aryl, heterocycle, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and
 c) $C_1$–$C_6$ alkyl unsubstituted or substituted by aryl, heterocycle, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
 a) hydrogen,
 b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}OC(O)$—, $R^{10}OC(O)$—, $N_3$, —$N(R^{10})_2$, or $R^{11}OC(O)NR^{10}$—, and
 c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is selected from hydrogen, $C_1$–$C_6$ alkyl, benzyl and aryl;

$R^{11}$ is selected from $C_1$–$C_6$ alkyl and aryl;

$A^1$ and $A^2$ are independently selected from: a bond, —CH=CH—, —C≡C—, —C(O)—, —C(O)NR^{10}—, —NR^{10}C(O)—, O, —N(R^{10})—, —S(O)_2N(R^{10})—, —N(R^{10})S(O)_2—, or $S(O)_m$;

Q is selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
 c) unsubstituted or substituted $C_1$–$C_6$ alkyl wherein the substitutent on the substituted $C_1$–$C_6$ alkyl is selected from unsubstituted or substituted aryl, heterocyclic, halogen $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

V is an aryl;

W is selected from:
 a) hydrogen, or
 b) $CF_3$;

X is —$CH_2$— or —$C(=O)$;

Z is selected from imidazolyl or pyridinyl;

m is 0, 1 or 2;

n is 0, 1, 2, 3 or 4;

p is 0, 1, 2, 3 or 4; and r is 1 to 5;
or the pharmaceutically acceptable salts thereof.

3. A pharmaceutical composition comprising a pharmaceutical carrier, and dispersed therein, a therapeutically effective amount of a compound of claim 1.

4. A pharmaceutical composition comprising a pharmaceutical carrier, and dispersed therein, a therapeutically effective amount of a compound of claim 2.

5. A method of inhibiting farnesyl-protein transferase which comprises administering to a mammal in need thereof a therapeutically effective amount of a pharmaceutical composition comprising a pharmaceutical carrier, and dispersed therein, a therapeutically effective amount of a compound of formula I:

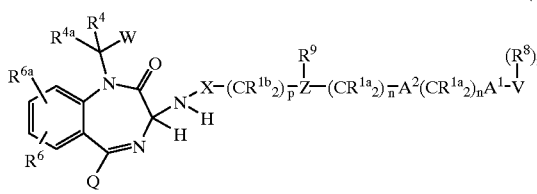

wherein
$R^{1a}$ and $R^{1b}$ are independently selected from:
   a) hydrogen,
   b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $NO_2$, $(R^{10})_2N$—C(NR$^{10}$)—, $R^{10}C(O)$—, $R^{10}OC(O)$—, $N_3$, —N(R$^{10}$)$_2$, or $R^{11}OC(O)NR^{10}$—,
   c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—C(NR$^{10}$)—, $R^{10}C(O)$—, $R^{10}OC(O)$—, $N_3$, —N(R$^{10}$)$_2$, and $R^{11}OC(O)$—NR$^{10}$—;

$R^4$ and $R^{4a}$ are independently selected from:
   a) hydrogen,
   b) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—C(NR$^{10}$)—, $R^{10}C(O)$—, $R^{10}OC(O)$—, $N_3$, —N(R$^{10}$)$_2$, and $R^{11}OC(O)$—NR$^{10}$—;

$R^6$ and $R^{6a}$ are independently selected from:
   a) hydrogen,
   b) halogen,
   c) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—C(NR$^{10}$)—, $R^{10}C(O)$—, $R^{10}OC(O)$—, $N_3$, —N(R$^{10}$)$_2$, and $R^{11}OC(O)$—NR$^{10}$—;

$R^8$ is selected from:
   a) hydrogen,
   b) aryl, heterocycle, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}_2N$—C(NR$^{10}$)—, $R^{10}C(O)$—, $R^{10}OC(O)$—, $N_3$, —N(R$^{10}$)$_2$, or $R^{11}OC(O)NR^{10}$—, and
   c) $C_1$–$C_6$ alkyl unsubstituted or substituted by aryl, heterocycle, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—C(NH)—, $R^{10}C(O)$—, $R^{10}OC(O)$—, $N_3$, —N(R$^{10}$)$_2$, or $R^{10}OC(O)NH$—;

$R^9$ is selected from:
   a) hydrogen,
   b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—C—(NR$^{10}$)—, $R^{10}C(O)$—, $R^{10}OC(O)$—, $N_3$, —N(R$^{10}$)$_2$, or $R^{11}OC(O)NR^{10}$—, and
   c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—C(NR$^{10}$)—, $R^{10}C(O)$—, $R^{10}OC(O)$—, $N_3$, —N(R$^{10}$)$_2$, or $R^{11}OC(O)NR^{10}$—;

$R^{10}$ is selected from hydrogen, $C_1$–$C_6$ alkyl, benzyl and aryl;

$R^{11}$ is selected from $C_1$–$C_6$ alkyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

Q is selected from:
   a) hydrogen,
   b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $NO_2$, $(R^{10})_2N$—C(NR$^{10}$)—, $R^{10}C(O)$—, $R^{10}OC(O)$—, —N(R$^{10}$)$_2$, or $R^{11}OC(O)NR^{10}$—,
   c) unsubstituted or substituted $C_1$–$C_6$ alkyl wherein the substitutent on the substituted $C_1$–$C_6$ alkyl is selected from unsubstituted or substituted aryl, heterocyclic, halogen $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—C(O)—, CN, $(R^{10})_2N$—C(NR$^{10}$)—, $R^{10}C(O)$—, $R^{10}OC(O)$—, $N_3$, —N(R$^{10}$)$_2$, and $R^{11}OC(O)$—NR$^{10}$—;

V is selected from:
   a) heterocycle,
   b) aryl,

W is selected from:
   a) hydrogen, or
   b) $CF_3$;

X is —CH$_2$—, —C(=O)—, or —S(=O)$_m$—;

Z is a heterocycle, selected from imidazolyl, pyrrolidinyl, pyridinyl, pyridonyl, 2-oxopiperidinyl, quinolinyl or isoquinolinyl;

m is 0, 1 or 2;

n is 0, 1, 2, 3 or 4;

p is 0, 1, 2, 3 or 4; and r is 1 to 5;

or the pharmaceutically acceptable salts thereof.

6. A method for inhibiting farnesyl-protein transferase which comprises administering to a mammal in need thereof a therapeutically effective amount of a composition of claim 4.

7. A method of treating cancer which comprises administering to a mammal in need thereof a therapeutically effective amount of a pharmaceutical composition comprising a pharmaceutical carrier, and dispersed therein, a therapeutically effective amount of a compound of formula I:

(I)

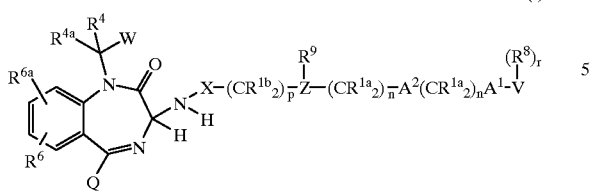

wherein $R^{1a}$ and $R^{1b}$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^4$ and $R^{4a}$ are independently selected from:
a) hydrogen,
b) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^6$ and $R^{6a}$ are independently selected from:
a) hydrogen,
b) halogen,
c) unsubstituted or substituted $C_1$–$C_6$ alkyl wherein the substitutent on the substituted $C_1$–$C_6$ alkyl is selected from halogen, unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

$R^8$ is selected from:
a) hydrogen,
b) aryl, heterocycle, cycloalkyl, alkenyl, alkynyl, perfluoroalkyl, F, Cl, Br, $R^{10}O$—, $R^{11}S(O)_m$—, $R^{10}C(O)NR^{10}$—, CN, $NO_2$, $R^{10}{}_2N$—$C(NR^{10})$—, $R^{10}C(O)$—, $R^{10}OC(O)$—, $N_3$, —$N(R^{10})_2$, or $R^{11}OC(O)NR^{10}$—, and
c) $C_1$–$C_6$ alkyl unsubstituted or substituted by aryl, heterocycle, cycloalkyl, alkenyl, alkynyl, perfluoroalkyl, F, Cl, Br, $R^{10}O$—, $R^{11}S(O)_m$—, $R^{10}C(O)NH$—, CN, $H_2N$—$C(NH)$—, $R^{10}C(O)$—, $R^{10}OC(O)$—, $N_3$, —$N(R^{10})_2$, or $R^{10}OC(O)NH$—;

$R^9$ is selected from:
a) hydrogen,
b) alkenyl, alkynyl, perfluoroalkyl, F, Cl, Br, $R^{10}O$—, $R^{11}S(O)_m$—, $R^{10}C(O)NR^{10}$—, CN, $NO_2$, $(R^{10})_2N$—$C$—$(NR^{10})$—, $R^{10}C(O)$—, $R^{10}OC(O)$—, $N_3$, —$N(R^{10})_2$, or $R^{11}OC(O)NR^{10}$—, and c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, CN, $(R^{10})_2N$—$C(NR^{10})$—, $R^{10}C(O)$—, $R^{10}OC(O)$—, $N_3$, —$N(R^{10})_2$, or $R^{11}OC(O)NR^{10}$—;

$R^{10}$ is selected from hydrogen, $C_1$–$C_6$ alkyl, benzyl and aryl;

$R^{11}$ is selected from $C_1$–$C_6$ alkyl and aryl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

Q is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—,
c) unsubstituted or substituted $C_1$–$C_6$ alkyl wherein the substitutent on the substituted $C_1$–$C_6$ alkyl is selected from unsubstituted or substituted aryl, heterocyclic, halogen $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2N$—$C(O)$—, CN, $(R^{10})_2N$—$C(NR^{10})$—, $R^{10}C(O)$—, $R^{10}OC(O)$—, $N_3$, —$N(R^{10})_2$, and $R^{11}OC(O)$—$NR^{10}$—;

V is selected from:
a) heterocycle,
b) aryl,

W is selected from:
a) hydrogen, or
b) $CF_3$;

X is —$CH_2$—, —$C(=O)$—, or —$S(=O)_m$—;

Z is a heterocycle, selected from imidazolyl, pyrrolidinyl, pyridinyl, pyridonyl, 2-oxopiperidinyl, quinolinyl or isoquinolinyl;

m is 0, 1 or 2;

n is 0, 1, 2, 3 or 4;

p is 0, 1, 2, 3 or 4; and r is 1 to 5;

or the pharmaceutically acceptable salts thereof.

8. A method for treating cancer which comprises administering to a mammal in need thereof a therapeutically effective amount of a composition of claim 4.

9. A method for treating neurofibromin benign proliferative disorder which comprises administering to a mammal in need thereof a therapeutically effective amount of a composition of claim 3.

10. A method for treating blindness related to retinal vascularization which comprises administering to a mammal in need thereof a therapeutically effective amount of a composition of claim 3.

11. A method for treating infections from hepatitis delta and related viruses which comprises administering to a mammal in need thereof a therapeutically effective amount of a composition of claim 3.

12. A method for preventing restenosis which comprises administering to a mammal in need thereof a therapeutically effective amount of a composition of claim 3.

13. A method for treating polycystic kidney disease which comprises administering to a mammal in need thereof a therapeutically effective amount of a composition of claim 4.

* * * * *